United States Patent
Wiebe et al.

(10) Patent No.: US 11,097,157 B2
(45) Date of Patent: Aug. 24, 2021

(54) ADAPTIVE CALIBRATION FOR SENSOR-EQUIPPED ATHLETIC GARMENTS

(71) Applicant: Mad Apparel, Inc., Redwood City, CA (US)

(72) Inventors: Christopher John Wiebe, Burlingame, CA (US); Seunghee Jang, San Francisco, CA (US); Dhananja Pradhan Jayalath, San Francisco, CA (US); Ankit Gordhandas, Sunnyvale, CA (US)

(73) Assignee: Mad Apparel, Inc., Redwood City, CA (US)

( * ) Notice: Subject to any disclaimer, the term of this patent is extended or adjusted under 35 U.S.C. 154(b) by 165 days.

(21) Appl. No.: 15/762,542

(22) PCT Filed: Dec. 16, 2016

(86) PCT No.: PCT/US2016/067372
§ 371 (c)(1),
(2) Date: Mar. 22, 2018

(87) PCT Pub. No.: WO2017/106781
PCT Pub. Date: Jun. 22, 2017

(65) Prior Publication Data
US 2019/0076699 A1   Mar. 14, 2019

Related U.S. Application Data

(63) Continuation of application No. 15/381,037, filed on Dec. 15, 2016, now abandoned.
(Continued)

(51) Int. Cl.
*A61B 5/02* (2006.01)
*A63B 24/00* (2006.01)
(Continued)

(52) U.S. Cl.
CPC .......... *A63B 24/0062* (2013.01); *A41D 1/002* (2013.01); *A61B 5/0004* (2013.01);
(Continued)

(58) Field of Classification Search
CPC ......... G16Z 99/00; G06F 19/00; G06F 1/163; A61B 5/0004; A61B 5/0022;
(Continued)

(56) References Cited

U.S. PATENT DOCUMENTS

| 6,623,427 | B2 | 9/2003 | Mandigo |
| 9,445,759 | B1 | 9/2016 | Lamego et al. |

(Continued)

FOREIGN PATENT DOCUMENTS

| WO | WO 91/011221 A1 | 8/1991 |
| WO | WO 91-252449 * | 8/1991 |
| WO | WO 2016/149751 A1 | 9/2016 |

OTHER PUBLICATIONS

PCT International Search Report and Written Opinion, PCT Application No. PCT/US2016/067372, dated Apr. 12, 2017, 24 pages.
(Continued)

*Primary Examiner* — Rex R Holmes
(74) *Attorney, Agent, or Firm* — Fenwick & West LLP

(57) ABSTRACT

An exercise feedback system receives a first set of physiological data from a garment worn by a user and user information from a client device of the user, the first set of physiological data describing muscle activation of a plurality of muscles of the user while performing a calibration workout. The exercise feedback system determines a calibration value based at least in part on the first set of physiological data and the user information. When the exercise feedback system receives a second set of physiological data describing muscle activation of the plurality of muscles while performing a subsequent workout from the
(Continued)

garment, the exercise feedback system modifies the calibration value based on the second set of physiological data. The exercise feedback system provides biofeedback generated based on the modified calibration value to the user via the client device.

21 Claims, 8 Drawing Sheets

Related U.S. Application Data

(60) Provisional application No. 62/269,391, filed on Dec. 18, 2015.

(51) Int. Cl.
| | | |
|---|---|---|
| *A61B 5/00* | (2006.01) | |
| *A61B 5/0205* | (2006.01) | |
| *A61B 5/11* | (2006.01) | |
| *G06F 1/16* | (2006.01) | |
| *G09B 19/00* | (2006.01) | |
| *H04Q 9/00* | (2006.01) | |
| *G16Z 99/00* | (2019.01) | |
| *A61B 5/316* | (2021.01) | |
| *A61B 5/389* | (2021.01) | |
| *A41D 1/00* | (2018.01) | |
| *A61B 5/024* | (2006.01) | |
| *A61B 5/0245* | (2006.01) | |
| *A61B 5/0531* | (2021.01) | |
| *G06F 19/00* | (2018.01) | |
| *A61B 5/318* | (2021.01) | |

(52) U.S. Cl.
CPC .......... *A61B 5/0022* (2013.01); *A61B 5/0205* (2013.01); *A61B 5/0245* (2013.01); *A61B 5/02055* (2013.01); *A61B 5/02438* (2013.01); *A61B 5/0531* (2013.01); *A61B 5/1118* (2013.01); *A61B 5/316* (2021.01); *A61B 5/389* (2021.01); *A61B 5/486* (2013.01); *A61B 5/6804* (2013.01); *A61B 5/7264* (2013.01); *A63B 24/0075* (2013.01); *G06F 1/163* (2013.01); *G06F 19/00* (2013.01); *G09B 19/003* (2013.01); *G09B 19/0038* (2013.01); *G16Z 99/00* (2019.02); *H04Q 9/00* (2013.01); *A61B 5/0015* (2013.01); *A61B 5/318* (2021.01); *A61B 5/7203* (2013.01); *A61B 2503/10* (2013.01); *A61B 2560/0223* (2013.01); *A61B 2562/0209* (2013.01); *A61B 2562/18* (2013.01); *A63B 2024/0068* (2013.01); *A63B 2220/836* (2013.01); *A63B 2230/06* (2013.01); *G08C 2201/93* (2013.01); *H04Q 2209/40* (2013.01); *H04Q 2209/86* (2013.01)

(58) Field of Classification Search
CPC .............. A61B 5/0205; A61B 5/02055; A61B 5/04012; A61B 5/1118; A61B 5/02438; A61B 5/0245; A61B 5/0488; A61B 5/0531; A61B 5/486; A61B 5/6804; A61B 5/7264; A61B 5/7203; A61B 5/0015; A61B 5/0402; A61B 2560/0223; A61B 2562/0209; A61B 2562/18; A61B 2503/10; G09B 19/0038; G09B 19/003; H04Q 9/00; H04Q 2209/40; H04Q 2209/86; A63B 24/0062; A63B 24/0075; A63B 2024/0068; A63B 2220/836; A63B 2230/06

See application file for complete search history.

(56) References Cited

U.S. PATENT DOCUMENTS

| | | |
|---|---|---|
| 9,720,515 B2 | 8/2017 | Wagner et al. |
| 10,065,074 B1 | 9/2018 | Hoang et al. |
| 10,357,688 B2 | 7/2019 | Wiebe et al. |
| 10,362,993 B2 | 7/2019 | Wiebe et al. |
| 2005/0107719 A1* | 5/2005 | Arad (Abbound) . A61B 5/0536 600/547 |
| 2005/0177059 A1 | 8/2005 | Koivumaa et al. |
| 2006/0136173 A1 | 6/2006 | Case et al. |
| 2007/0232453 A1 | 10/2007 | Hanoun |
| 2008/0262392 A1* | 10/2008 | Ananny ............. A63B 24/0062 600/595 |
| 2009/0171233 A1 | 7/2009 | Lanfermann et al. |
| 2010/0268477 A1 | 10/2010 | Mueller et al. |
| 2010/0312508 A1 | 12/2010 | Mott et al. |
| 2012/0004696 A1 | 1/2012 | Sun et al. |
| 2012/0071732 A1 | 3/2012 | Grey et al. |
| 2012/0143093 A1 | 6/2012 | Stirling et al. |
| 2012/0271143 A1 | 10/2012 | Aragones et al. |
| 2013/0041590 A1 | 2/2013 | Bunch et al. |
| 2013/0136301 A1 | 5/2013 | Abrahamsson et al. |
| 2014/0135593 A1* | 5/2014 | Jayalth ................. A61B 5/6805 600/301 |
| 2014/0142459 A1 | 5/2014 | Jayalth et al. |
| 2014/0235965 A1 | 8/2014 | Tran |
| 2014/0318699 A1 | 10/2014 | Longinotti-Buitoni et al. |
| 2014/0378858 A1 | 12/2014 | Armitage et al. |
| 2015/0088284 A1 | 3/2015 | Hendricks et al. |
| 2015/0120016 A1* | 4/2015 | Houmanfar .......... A61B 5/7267 700/91 |
| 2015/0148619 A1 | 5/2015 | Berg et al. |
| 2015/0230719 A1 | 8/2015 | Berg et al. |
| 2015/0272482 A1 | 10/2015 | Houmanfar et al. |
| 2015/0272483 A1 | 10/2015 | Etemad et al. |
| 2015/0272501 A1 | 10/2015 | MacEachern et al. |
| 2015/0282768 A1* | 10/2015 | Luna ...................... A61B 5/721 600/301 |
| 2015/0309563 A1 | 10/2015 | Connor |
| 2015/0351690 A1 | 12/2015 | Toth et al. |
| 2015/0366504 A1 | 12/2015 | Connor |
| 2016/0038083 A1 | 2/2016 | Ding et al. |
| 2017/0071548 A1 | 3/2017 | Wiebe et al. |
| 2017/0173391 A1 | 6/2017 | Wiebe et al. |
| 2018/0133551 A1 | 5/2018 | Chang et al. |
| 2018/0140901 A1 | 5/2018 | Wiebe et al. |
| 2018/0140902 A1 | 5/2018 | Wiebe et al. |
| 2019/0029594 A1 | 1/2019 | Jiang et al. |
| 2019/0046107 A1 | 2/2019 | Jang et al. |
| 2019/0046839 A1 | 2/2019 | Jang et al. |
| 2019/0076699 A1 | 3/2019 | Wiebe et al. |
| 2019/0282856 A1 | 9/2019 | Wiebe et al. |
| 2019/0290181 A1 | 9/2019 | Mrvaljevic et al. |
| 2019/0343459 A1 | 11/2019 | Korzinov et al. |
| 2019/0344121 A1 | 11/2019 | Wells et al. |

OTHER PUBLICATIONS

PCT Invitation to Pay Additional Fees, PCT Application No. PCT/US2016/067372, dated Jan. 30, 2017, 2 pages.
International Search Report and Written Opinion, PCT Application No. PCT/US2018/046565, dated Dec. 7, 2018, 18 pages.
Tank, P., Muscles of the Lower Limb, Department of Neurobiology and Developmental Sciences, University of Arkansas for Medical Sciences, 2009, retrieved online from http://anatomy.uams.edu/muscles_lowerlimb.html on Oct. 30, 2020, 9 pages.

* cited by examiner

ADAPTIVE CALIBRATION FOR SENSOR-EQUIPPED ATHLETIC GARMENTS

CROSS-REFERENCE TO RELATED APPLICATIONS

This application is a national stage application under 35 U.S.C. § 371 of PCT Application No. PCT/US2016/067372, filed Dec. 16, 2016 and published as WO2017106781A1, which claims the benefit of and priority to U.S. Provisional Application No. 62/269,391 filed Dec. 18, 2015; and U.S. Patent Publication No. 2017/0173391 A1 and filed Dec. 15, 2016, which are each incorporated by reference herein in its entirety. The subject matter of the present application is related to U.S. Pat. No. 10,357,688B2, granted on Jul. 23, 2019, entitled "Exercise Biofeedback Using Sensor-Equipped Athletic Garments," the entire disclosure of which is incorporated herein by reference.

BACKGROUND

This description generally relates to sensor-equipped athletic garments, and specifically to calibrating sensors of the athletic garments.

Sensors record a variety of information about the human body. For example, electrocardiograph (ECG) electrodes can measure electrical signals from the skin of a person that are used to determine the person's heart rate. In addition, electromyography (EMG) electrodes can measure electrical activity generated by a person's muscles. Heart rate and muscle activation information may be useful for evaluating the person's physiological condition, for instance, while exercising.

The electrical signals measured by sensors such as ECG or EMG electrodes on a person's body may vary based on several factors. For example, a leg muscle may generate more electrical activity on average than an arm muscle because there are more muscle fibers in the leg muscle. As another example, the sensors generate different physiological data for a male adult than a female child because the male adult has larger muscles. Thus, it is difficult to provide comparable metrics between different muscle groups for a given person and between different people since the muscle response depends on muscle physiology and body composition, which may vary between muscles and between people.

Signal responses of the electrical activity from sensors can vary greatly across different muscle groups for a given person and between people. In particular, when measuring the EMG electrical signal from the surface of the body, different muscle groups could have different signal amplitude ranges that correspond to the range of contraction intensity of the muscle. The EMG signal measured at a given muscle depends on the physiology of the muscle A system that generates metrics of a person's athletic performance based on inconsistent calibration results from the physiological data can provide a poor user experience. With inaccurate calibration results, one muscle group could be reported to have an activation level that is inaccurate with respect to another muscle group or when comparing to another person. In particular, if the metrics indicate inaccurate values for the person's muscle activation or heart rate, the person may lose confidence in the reliability of the system.

SUMMARY

An exercise feedback system calibrates sensors of an athletic garment worn by an athlete while performing exercises. The sensors can record physiological data such as EMG signals that represent muscle activation, which is a measure of the athlete's muscle exertion during an exercise. The exercise feedback system instructs the athlete to perform calibration exercises, for instance, when the athlete begins using the exercise feedback system during an onboarding phase. The exercise feedback system generates a calibration value based on physiological data from the calibration exercises. For instance, the calibration value indicates the predicted maximum amplitude for the muscle activation of a particular muscle group (for example, glutes, hamstrings, or quadriceps) of the athlete. The calibration values may account for variations in the physiological data across different muscles or athletes. Example factors that may contribute to the variations include user demographics, muscle physiology, body composition, sensor contact quality, fatigue, etc.

During the onboarding phase, the exercise feedback system can also determine initial calibration values based on information about the athlete such as demographic data or known performance metrics. During an ongoing phase after the onboarding phase, the exercise feedback system can refine the calibration value over time as the system receives additional physiological data from subsequent exercises performed by the athlete and/or information describing exercise context. The ongoing phase may include multiple sub-phases. For example, during a first phase (e.g., after the first five workouts completed by the athlete), the exercise feedback system performs an initial refinement of the calibration values, and may reprocess physiological data from the first phase. During a second or subsequent phase, the exercise feedback system continues to refine the calibration values as the system receives additional data from the athlete's workouts. The exercise feedback system determines a confidence level of the calibration value and may update the calibration value if the confidence level becomes too low. In some embodiments, the exercise feedback system uses a trained machine learning model to determine and/or update the calibration value and confidence level. The exercise feedback system provides biofeedback to the athlete generated during the performance of subsequent activity and based on the calibration value. For example, the biofeedback indicates a percentage of muscle activation relative to the calibration value for the particular muscle groups. In one embodiment, contribution between different muscle groups can therefore be accurately compared given that the calibration value between different muscle groups accurately reflects the same level of contraction intensity and the relationship between signal amplitude and muscle activation is comparable. In another example, the biofeedback may be based on an increase or decrease in the calibration value over time, e.g., representing changes in strength or physiology of the athlete related to the athlete's training.

In one embodiment when providing feedback to a person regarding muscle utilization during training, it can be important to be able to compare the response from different muscle groups. As explained above, for a given contraction intensity, two different muscle groups could have different amplitude signal responses. Embodiments of the disclosed invention include a process for transforming the EMG signal response to a common scale to provide biofeedback that allows for the comparison of different muscle groups within an individual and across people.

Existing systems (e.g., within an academic setting) propose calibrating an EMG signal response from a given muscle. This process may be referred to as normalizing. Prior calibration approaches generally require specific equipment and have been developed to normalize measurements for a specific muscle across multiple trials where the electrodes are re-applied to a subject person. In an example use case, a desired outcome is to reduce measurement differences for a given muscle across trials. Embodiments of the disclosed invention include a calibration process that accounts for the unique challenges of a consumer product. In one embodiment, a process provides an initial calibration value to the athlete when first using a product associated with the exercise feedback system and continues to refine the calibration values over time with additional physiological data and context from the athlete. The process can leverage data collected on the athlete over multiple training sessions and multiple different types of input to improve calibration accuracy. The process can also leverage context collected from the athlete during those training sessions including the exercise performed, reps, weight, or any other performance benchmarks (e.g. time, distance, etc.).

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. System Overview

Figure 1:
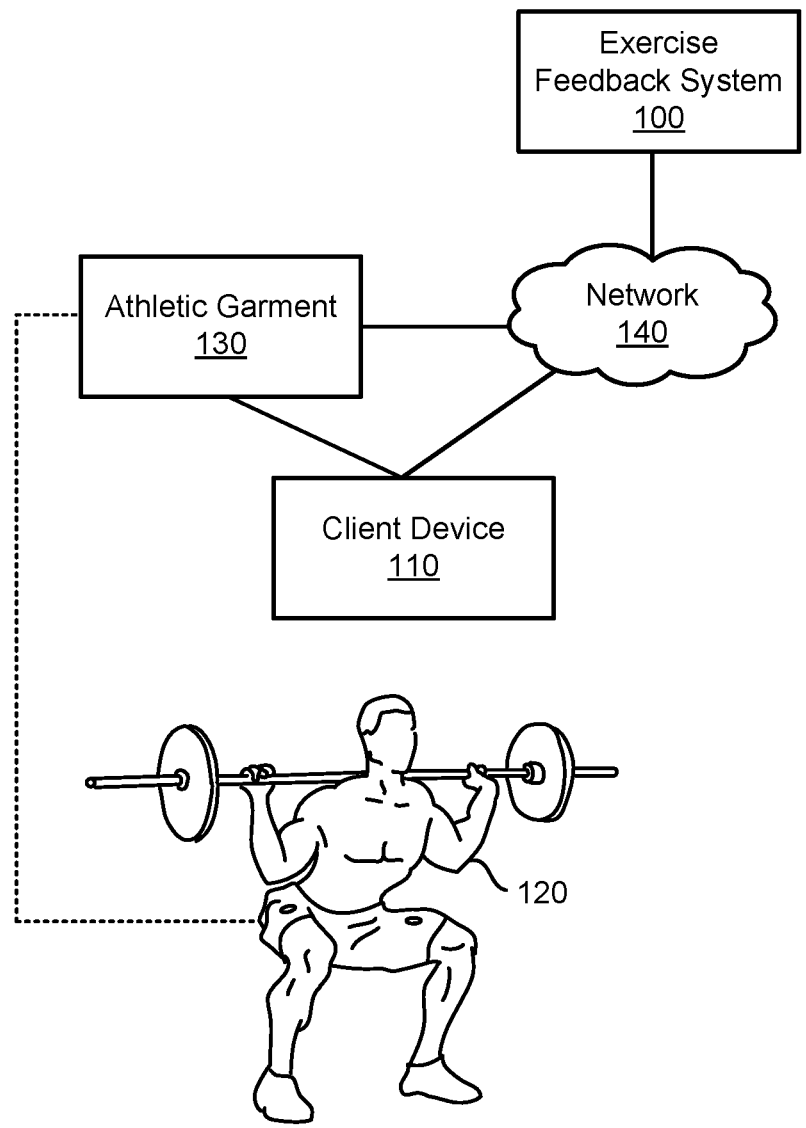
FIG. 1 is a diagram of a system environment for monitoring exercise data according to one embodiment.

FIG. 1 is a diagram of a system environment for monitoring exercise data according to one embodiment. The system environment includes an exercise feedback system 100, client device 110, and athletic garment 130 communicatively coupled together via a network 140. Users of the exercise feedback system 100 are also referred to herein as "athletes." In other embodiments, different and/or additional entities can be included in the system architecture.

The client device 110 is a computing device capable of receiving user input as well as transmitting and/or receiving data via the network 140. A client device is a device having computer functionality, such as a smartphone, personal digital assistant (PDA), a mobile telephone, tablet, laptop computer, desktop computer, or another suitable device. In one embodiment, a client device executes an application allowing a user of the client device to interact with the exercise feedback system 100. For example, a client device executes a browser application to enable interaction between the client device and the exercise feedback system 100 via the network 140. In another embodiment, a client device interacts with the exercise feedback system 100 through an application programming interface (API) running on a native operating system of the client device, such as IOS® or ANDROID™.

The network 140 includes any combination of local area and/or wide area networks, including both wired and/or wireless communication systems. In one embodiment, the network 140 uses standard communications technologies and/or protocols. For example, the network 140 includes communication links using technologies such as Ethernet, 802.11, worldwide interoperability for microwave access (WiMAX), 3G, 4G, code division multiple access (CDMA), digital subscriber line (DSL), BLUETOOTH®, Wi-Fi, ZIGBEE®, other suitable close-range networks, etc. Examples of networking protocols used for communicating via the network 140 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 140 may be represented using any suitable format, such as hypertext markup language (HTML) or extensible markup language (XML). In some embodiments, all or some of the communication links of the network 140 may be encrypted using any suitable technique or techniques.

An athlete 120 wears the athletic garment 130 while performing exercises. The athletic garment 130 records physiological data, e.g., muscle activation data or heart rate data, of the athlete. Based on the physiological data, the exercise feedback system 100 generates exercise feedback customized for the athlete. Further, a coach of the athlete can view the exercise feedback on a client device and provide additional feedback for the athlete. The athlete can view the exercise feedback and any additional feedback displayed on a user interface of the client device 110. In some embodiments, the exercise feedback system 100 can communicate the exercise feedback using audio output or haptic feedback of the client device 110.

II. Athletic Garment

Figure 2:
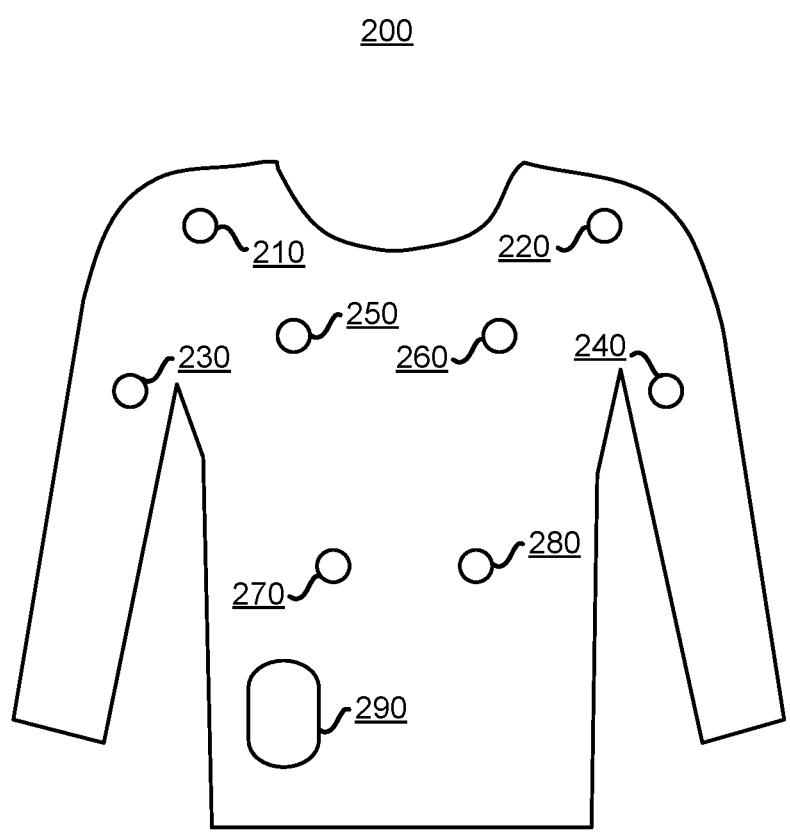
FIG. 2 is a diagram of a sensor-equipped athletic garment according to one embodiment.

FIG. 2 is a diagram of a sensor-equipped athletic garment 200 according to one embodiment. The athletic garment 200 includes sensors that contact the skin of an athlete wearing the athletic garment 200. For example, the sensors can be electrodes that measure electromyography (EMG) signals (electrical signals caused by muscle cells) also referred to as muscle activation data or muscle activation levels, electrocardiograph (ECG) signals (electrical signals caused by depolarization of the user's heart muscle in particular) also referred to as heart rate data, electrical signals modified by the tissue of the user (also referred to herein as bioimpedance data), electroencephalograph (EEG) signals, magnetoencephalograph (MEG) signals, among other types of signals associated with physiological data. The sensors may also include other types of sensors such as accelerometers and gyroscopes (which generate motion data based on the athlete's movement), temperature sensors, pressure sensors, humidity sensors, geographical location sensors, etc. The sensors generate physiological data of the athlete based on the measured signals. The sensors are communicatively coupled to a processing unit 290. The processing unit 290 can aggregate and analyze the physiological data from the sensors. The processing unit 290 can also provide the physiological data to the client device 110 or exercise feedback system 100 via the network 140.

In the embodiment shown in FIG. 2, the athletic garment 200 includes eight sensors that record muscle activation data from the athlete's muscles nearby each sensor. In particular, sensors 210 and 220 located on the right and left shoulder of the athletic garment 200 can record muscle activation data of the athlete's deltoid muscles. Sensors 230 and 240 located on the right and left sleeves of the athletic garment 200 can record muscle activation data of the athlete's triceps and/or bicep muscles. Sensors 250 and 260 located on the right and left chest of the athletic garment 200 can record muscle activation data of the athlete's pectoral muscles. Sensors 270 and 280 located on the right and left abdomen of the athletic garment 200 can record muscle activation data of the athlete's abdominal and oblique muscles. Though the athletic garment 200 shown in FIG. 2 includes eight sensors and the processing unit 290, in other embodiments, the athletic garment 200 can include any number of sensors or other types of components or electronics at any location or configuration within the athletic garment 200.

It should be noted that while the athletic garment 200 shown in FIG. 2 is a long sleeve shirt, the principles described herein apply equally to any garment, including but not limited to a short sleeved shirt, a tank top, pants, shorts (e.g., the athletic garment 130 shown in FIG. 1), or any other suitable garment. In embodiments where the athletic garment is a pant or shorts, sensors of the athletic garment can record muscle activation data from muscles on an athlete's lower body, e.g., quadriceps, gluteus maximus (also referred to herein as "glutes"), hamstrings, calves, and the like.

III. Exercise Feedback System

Figure 3A:
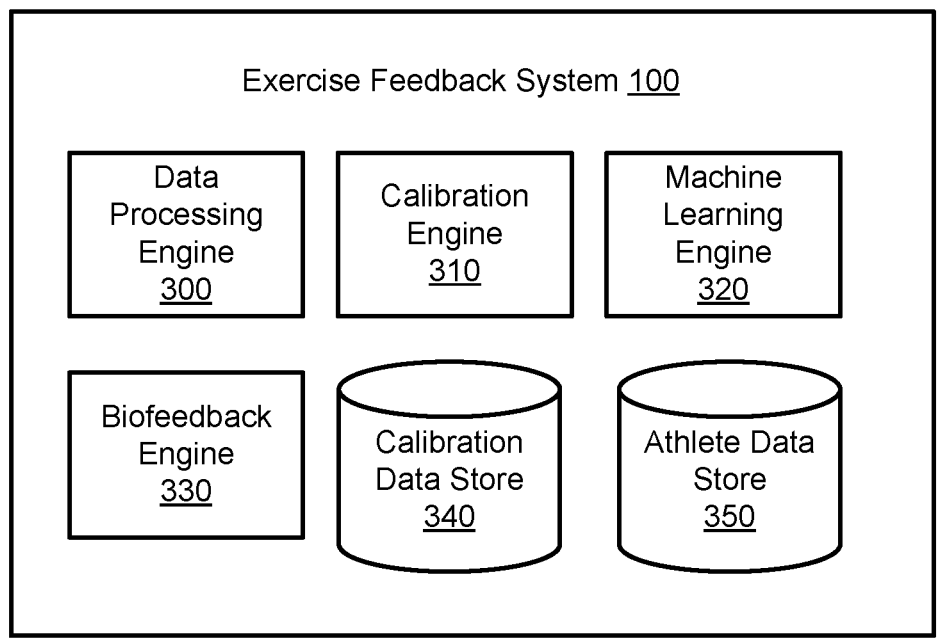
FIG. 3A is a block diagram of an exercise feedback system according to one embodiment.

FIG. 3A is a block diagram of the exercise feedback system 100 according to one embodiment. The exercise feedback system 100 includes a data processing engine 300, calibration engine 310, machine learning engine 320, biofeedback engine 330, calibration data store 340, and athlete data store 350. In other embodiments, the exercise feedback system 100 may include additional, fewer, or different components for various applications, which are not shown so as to not obscure the details of the system architecture.

The data processing engine 300 processes physiological data generated by sensors of an athletic garment, e.g., athletic garment 200 shown in FIG. 2. The exercise feedback system 100 can receive the physiological data from the client device 110 or the processing unit 290 of the athletic garment 200. The data processing engine 300 can process the physiological data by performing noise filtering or feature extraction. Example noise filtering techniques include a moving average filter, root mean square condition, standard deviation, low pass, high pass, band pass, and notch filters. Features can include a heart rate or level of muscle activation for a certain muscle of an athlete. For example, the data processing engine 300 determines the heart rate, e.g., in beats per minute, of an athlete based on the frequency of a sample of sinusoidal heart rate data. In another example, the data processing engine 300 determines a level of muscle activation for a particular muscle of an athlete based on the amplitude of muscle activation data from EMG signals.

Physiological data generated by sensors of the athletic garment may vary based on parameters associated with the athlete wearing the athletic garment, e.g., based on the body composition of the athlete. The physiology of the muscle influences the muscle activation data associated with contraction of the muscle. For example, the number of muscle fibers, fiber size and fiber type distribution (e.g., slow twitch or fast twitch) can influence the muscle activation signal amplitude associated with the muscle group. Also, the thickness of adipose tissue between the muscle tissue and skin surface may influence the amplitude of the muscle activation signal generated by sensors of the athletic garment. For instance, the amplitude of muscle activation data may be proportional to the muscle fiber size and/or inversely proportional to the amount of fat between the muscle and the portion of skin.

Physiological data generated by sensors of the athletic garment may also vary based on parameters associated with the different types of muscles contacting the sensors, e.g., based on the local and/or global body composition of the athlete. For example, muscles include a combination of slow twitch muscle fibers and fast twitch muscle fibers. During an exercise, a ratio of activated fast twitch muscle fibers to activated slow twitch muscle fibers depends on the athlete's intensity of contraction of the muscle. For instance, as the athlete contracts the muscle with greater exertion, additional fast twitch muscle fibers are activated. Therefore, the change in muscle contraction intensity changes the ratio of activated types of muscle fibers and ultimately may manifest as a difference in amplitude of muscle activation data generated between sensors contacting different muscle groups.

The data processing engine 300 may also correlate body composition information with other types of sensor data, e.g., correlating body fat percentage with heart rate data. The amplitude of muscle activation data associated with a first muscle group may be greater than the amplitude of muscle activation data associated with a second muscle group due to variations in any of the above parameters and/or other factors. Additional example parameters include muscle fiber size, muscle fiber distribution, and the amount of fat between a muscle and a portion of skin contacting the sensor.

Additionally, physiological data generated by sensors of the athletic garment may vary because athletes have different physiological traits, such as muscle fiber size, body composition, and other traits similar to those that cause differences in muscle activation data across different muscle groups. For instance, a 25 year-old male athlete who is a professional swimmer may have an average amplitude of muscle activation data greater than that of a 10 year-old female athlete for a given muscle contraction intensity. The physiological data may also vary based on the sensor contact quality. For example, thicker hair on the athlete's skin or skin dryness may result in poor sensor contact quality, and thus reduce the amplitude of physiological data generated by the sensors. As another example, skin oiliness or sweat may result in improved sensor contact quality, and thus increase the amplitude of physiological data generated by the sensors. Similar to processing physiological data based on body composition data, for example, the data processing engine 300 may determine sensor contact quality (e.g., a level of physical contact with the skin) based on bioimpedance data generated by a sensor. The data processing engine 300 may also correlate the sensor contact quality and/or bioimpedance data with other types of sensor data (e.g., heart rate information). In some embodiments, the amplitude of physiological data generated by a sensor is inversely proportional to the impedance between the sensor and the skin of the athlete.

In some embodiments, the bioimpedance data varies based on both a level of contact between the sensor and athlete's body as well as the body tissue of the athlete. A data signal generated by sensors (or other electrical components) of the athletic garment varies based on the body tissue. Based on parameters of the bioimpedance data, the data processing engine 300 may determine the athlete's body composition at the multiple locations on the athlete's body that correspond to the location of the sensors. Different compositions of muscle and fat tissue will change characteristics of the bioimpedance data signal. The data processing engine 300 may improve the accuracy of calibration values (e.g., generated by the calibration engine 310 described below) corresponding to a given muscle location by using body composition data determined based on bioimpedance data local to a sensor corresponding to a specific muscle group.

In one embodiment, the data processing engine 300 may measure an ECG signal corresponding to the heart function (e.g., heart rate or pulse) of the athlete using sensors of the athletic garment. Parameters of the ECG signal such as the amplitude or frequency may vary based on where the ECG signal is measured from on the athlete's body. Parameters of the ECG signal may also vary based on the tissue and body composition of the athlete at different locations on the body (e.g., on the chest, an arm, or a leg). Thus, the data processing engine 300 can determine the body composition on different portions of the athlete's body based on changes in the ECG signal parameters. The exercise feedback system 100 may improve the accuracy of calibration values based the body composition determined using the ECG signals.

The calibration engine 310 calibrates the exercise feedback system 100 to account for variations in physiological data across different muscles of an athlete and across different athletes. The calibration engine 310 normalizes physiological data of a set of muscles based on the amplitude of the muscle activation data, in one embodiment. The calibration engine 310 provides instructions that prompt an athlete wearing the athletic garment to perform one or more calibration exercises. The calibration exercises include, for example, activities that do not require any weights or equipment such as walking up stairs, jumping, standing, lying down, performing a leg raise, sprinting for a certain distance or duration of time, or moving a limb. The calibration exercises may also include activities that do require weights and/or other equipment such as performing a squat, bench press, overhead press, biceps curl, pull-up, or deadlift with a barbell. The calibration exercises may target one or more muscle groups, e.g., a chest fly, bent over row, arm curl, arm extension, arm raise, or push-up exercise target upper body muscles (e.g., pectorals, biceps, triceps, or deltoids), and a squat, kickback, or leg curl target lower body muscles (e.g., the quadriceps, glutes, or hamstrings). The calibration exercises may also target an isolated one or more muscles.

The instructions may prompt the athlete to perform a target number of repetitions of the calibration exercise. The instructions may also prompt the athlete to perform the calibration exercise based on the athlete's repetition maximum (which may also be referred to herein as "rep max" or RM) for a target number of repetitions of the calibration exercise. The repetition maximum represents the greatest amount of weight that the athlete can lift for a given number of repetitions, or in other words, the maximum voluntary contraction of a muscle of the athlete. In one embodiment, the calibration engine 310 provides the instructions to the athlete when the athlete starts using the exercise feedback system 100 so that the calibration engine 310 can determine calibration values personalized to the athlete before the athlete completes additional exercises using the exercise feedback system 100. The calibration engine 310 may also provide instructions to the athlete to perform calibration exercises at a future time, e.g., to determine updated calibration values. The calibration engine 310 can update calibration values over time as the calibration engine 310 receives additional physiological data from exercises and training programs that the athlete (or other athletes of the exercise feedback system 100) performs. In some embodiments, the calibration engine 310 may provide instructions to the athlete to input a level of perceived effort corresponding to a calibration exercise.

In one embodiment, the calibration engine 310 provides different calibration exercise options to the athlete. For example, a shorter option includes fewer calibration exercises than a longer option, and thus the athlete can complete the shorter option quickly to begin performing other workouts using the exercise feedback system 100. The longer option may require more time to complete, though may be advantageous because the calibration engine 310 may determine more accurate calibration values based on calibration exercises from the longer option, for example, because the calibration engine 310 receives a larger sample of physiological data. As one example, a shorter option includes one calibration exercise prompting the athlete to complete three repetitions of a squat exercise at the athlete's three repetition maximum. As a different example, a longer option includes squat, lunge, and pushup calibration exercises, where each calibration exercise involves five repetitions at the athlete's five repetition maximum.

In some embodiments, the calibration engine 310 determines calibration values without requiring the athlete to perform a calibration exercise. For example, the calibration data store 340 includes a database of reference calibration values associated with different parameters of athletes. Based on the information about a target athlete, the calibration engine 310 selects one or more reference calibration values from the database associated with parameters similar to those of the target athlete. For instance, the calibration values are associated with parameters such as demographic information (e.g., age, gender, height, weight, body composition, etc.), muscle type, exercise type, athlete skill level (e.g., a known performance metric such as personal records for certain exercises, vertical jump height, max number of pull-ups or push-ups, max wall-sit time, 1-mile run time, or 40-yard sprint time), health information (e.g., resting heart rate or heart rate while recovering after performing an exercise), genetics (e.g., associated with certain types of physiological traits), and the like. In one embodiment, the reference calibration value is based on an average of calibration values of a population of athletes with similar parameters, e.g., 20-30 year old female swimmers. The reference calibration values may be stored with a confidence level based on the variation of the calibration values of the population of athletes.

The machine learning engine 320 uses machine learning techniques to train one or more models for determining calibration values, in some embodiments. For example, a machine learning model can predict the maximum muscle activation level of an athlete corresponding to a number of input parameters of the athlete, as previously described above, e.g., including demographics and known performance metrics. Additionally, the machine learning model can predict the range of muscle activation levels (e.g., including an estimated maximum and minimum value) of an athlete corresponding to exercises completed by the athlete, the physiological data collected from those exercises, and/or additional information including the exercise type, weight, number of reps and athlete perceived effort. Further, the machine learning model can determine a confidence level of the predicted muscle activation level for the one rep max. In some embodiments, the calibration engine 310 uses the predicted maximum muscle activation level and confidence level to determine or to update calibration values. Machine learning techniques include, for example, supervised and unsupervised learning, linear regression, decision trees, support vector machines, classifiers (e.g., a Naive Bayes classifier), and gradient boosting, boosting for other algorithms (e.g., AdaBoost), neural net, logistic regression, and memory-based learning. The machine learning models can initially be trained by extracting features associated with calibration exercises, demographics and desired calibration levels completed by other athletes of the exercise feedback system 100. In some embodiments, after initial training, the machine learning model can be further trained to reduce the error of the predicted calibration level for the athletes in the training set.

The biofeedback engine 330 generates biofeedback for users of the exercise feedback system 100 based on features extracted by the data processing module 300 and calibration values determined by the calibration engine 300. The biofeedback indicates a metric of performance (e.g., a percentage value, a Boolean value such as satisfactory or unsatisfactory, or any suitable type of value) of an athlete performing exercises. As another example, the metric of performance may indicate a level of balance of the athlete while performing an exercise, e.g., whether the athlete's muscle activation levels for the left and right quads during a squat exercise are within a predetermined threshold value. The biofeedback may be associated with a particular muscle group, repetition of an exercise, set of an exercise (e.g., with multiple repetitions), workout, or session for a given day.

The biofeedback engine 330 can store the biofeedback in the athlete data store 350 along with information identifying the corresponding athlete. The biofeedback engine 330 can compare the extracted features with features based on reference exercise data from the athlete data store 350. In one example, the reference exercise data indicates a target range of one repetition maximum weight for a squat exercise based on demographic information of an athlete. If an athlete's one repetition maximum weight falls within the target range, the biofeedback engine 330 generates biofeedback indicating that the athlete has a satisfactory one repetition maximum weight for squat exercises. Further, by generating biofeedback based on calibration values, the biofeedback engine 330 can provide metrics that compare the performance between different muscle groups and between different athletes. Additional details regarding generating biofeedback are disclosed in U.S. patent application Ser. No. 15/356,354, filed on Nov. 18, 2016, the entire disclosure of which is incorporated herein by reference.

Figure 3B:
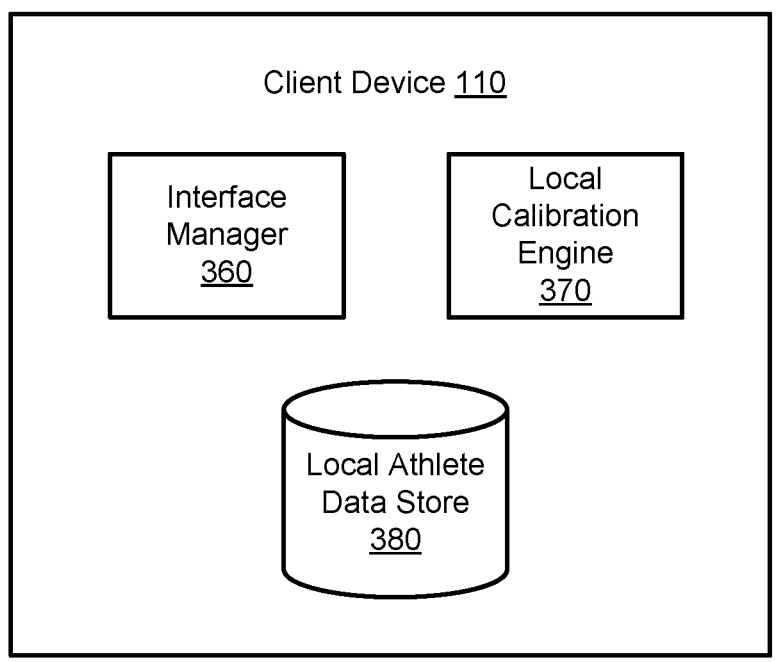
FIG. 3B is a block diagram of a client device according to one embodiment.

FIG. 3B is a block diagram of the client device 110 according to one embodiment. The client device 110 includes an interface manager 360, local calibration engine 370, and local athlete data store 380. In other embodiments, the client device 110 may include additional, fewer, or different components for various applications, which are not shown so as to not obscure the details of the system architecture.

In some embodiments, some or all of the functionality of the exercise feedback system 100 may be performed by or implemented within the client device 110. For example, the client device includes the local calibration engine 370 to provide instructions regarding calibration exercises to the athlete, determine (or update) calibration values, and store the calibration values in the local athlete data store 380. This can be advantageous because the client device 110 may not always have a network connection while an athlete is exercising (e.g., the athlete's gym does not have internet available). Thus, the calibration values are generated locally on the client device 110 without having to upload the physiological data to the exercise feedback system 100 for processing.

The interface manager 360 receives physiological data from the athletic garment 130 and can provide the physiological data to the exercise feedback system 100 for further processing. The interface manager 360 receives biofeedback, exercise training programs, and other information from the exercise feedback system 100. Based on the received information, the interface manager 360 may generate graphical user interfaces depicting the biofeedback, exercise training programs, calibration exercises, and the like. In some embodiments, the interface manager 360 presents the biofeedback and exercise training programs using audio or any other suitable form of feedback, e.g., vibrating the client device 110 as tactile feedback. The interface manager 360 can store physiological data, biofeedback, or exercise training programs in the local athlete data store 380.

The interface manager 360 can receive athlete information input by the athlete via the client device 110. The interface manager 360 can store the athlete information in the local athlete data store 380 or provide the athlete information to the exercise feedback system 100 to be stored in the athlete data store 350. The athlete information can describe, e.g., a goal of the athlete, demographic data, geographical location, one or more sports that the athlete plays, history of injuries of the athlete, other types of data such as biometrics including weight and height. Additionally, the interface manager 360 can receive information input by a coach of the athlete via a client device, and provide the input information to the exercise feedback system 100.

IV. Example Physiological Data

Figure 4:
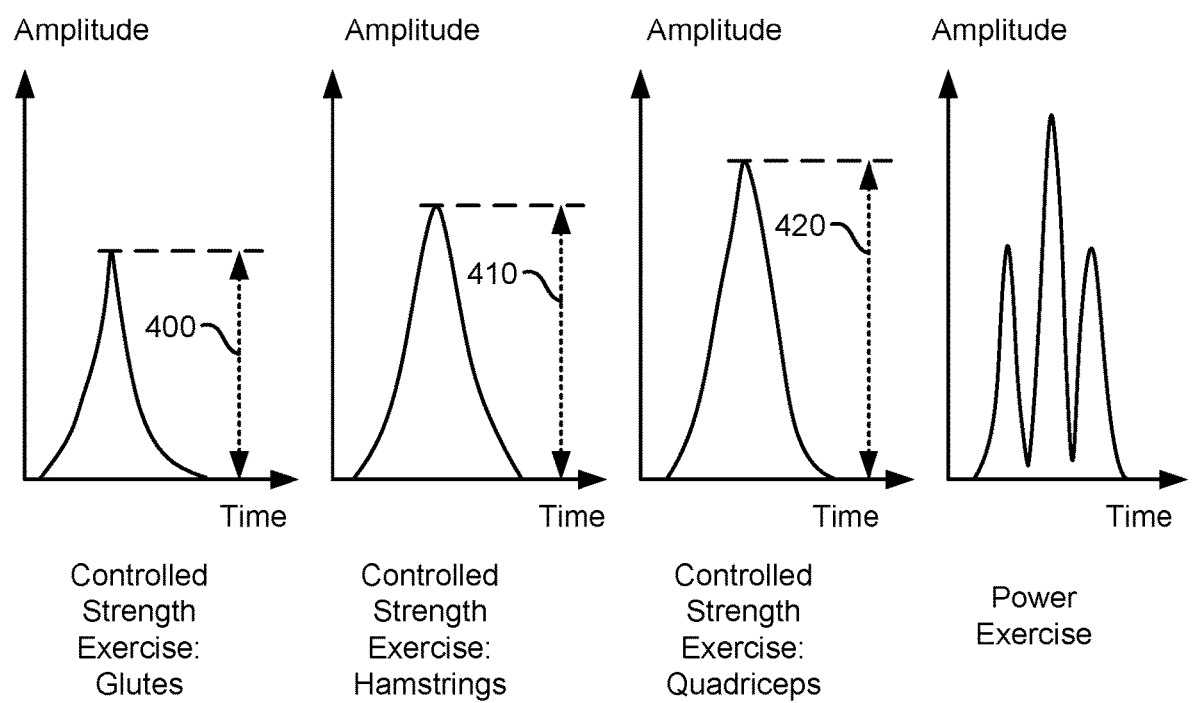
FIG. 4 shows graphs of physiological data associated with controlled strength exercises according to one embodiment.

FIG. 4 shows graphs of physiological data associated with controlled strength exercises according to one embodiment. The graphs show muscle activation data of the glutes, hamstrings, and quadriceps muscles for three separate controlled strength exercises performed by an athlete, as well as muscle activation data for a separate power exercise. The peak amplitude 420 for the quadriceps exercise is greater than the peak amplitude 410 for the hamstrings exercise, which is greater than the peak amplitude 400 for the glutes exercise. In one embodiment, the calibration engine 310 uses the peak amplitudes to calibrate the muscle activation data. The calibration engine 310 stores the peak amplitudes 400, 410, and 420 along with information identifying the glutes, hamstrings, and quadriceps muscles, respectively, in the calibration data store 350.

The biofeedback engine 330 generates biofeedback associated with the athlete's glutes, hamstrings, and quadriceps muscles based on the stored peak amplitudes, e.g., calibration values. For example, biofeedback engine 330 generates biofeedback indicating a percentage value representation of muscle activation level of the glutes muscle while the athlete is performing an exercise. The percentage value is relative to the peak amplitude 400. Similarly, the biofeedback engine 330 may generate biofeedback indicating a percentage value representation of muscle activation levels of the athlete's hamstrings and quadriceps muscles relative to the peak amplitudes 410 and 420, respectively. Thus, the calibration engine 310 can normalize physiological data across different types of muscles. In particular, though the glutes, hamstrings, and quadriceps muscles may each have different ranges of muscle activation levels, based on the calibration values, the biofeedback engine 330 generates biofeedback that presents the muscle activation levels for each of the three muscles on the same scale, e.g., as a percentage from 0% to 100%, which is a relative scale rather than an absolute scale. Thus, the peak amplitudes 400, 410, and 420 can each correspond to the same percentage of muscle activation, relative to the maximum amplitude for the glutes, hamstrings, and quadriceps, respectively, even though the three peak amplitude values have different magnitudes as shown in FIG. 4. Based on normalized physiological data, the biofeedback engine 330 can generate comparative metrics between different types of muscle groups or between muscles of different athletes. Further, the biofeedback engine 330 can generate biofeedback indicative of overall athletic performance of an athlete (e.g., full body metrics).

In some embodiments, the biofeedback engine 330 generates biofeedback based on data from other sources accessible to the exercise feedback system 100. For example, the exercise feedback system 100 receives images (or other types of media) of an athlete from a third party system (e.g., a social networking system). By processing the images of the athlete, the biofeedback engine 330 can generate a visualization (e.g., including overlaying depiction of muscles) of the athlete's body that is normalized to account for the athlete's body mass index (BMI).

In some embodiments, sensors of an athletic garment generate physiological data with less variation when an athlete performs controlled strength exercises than when the athlete performs power exercises. Controlled strength exercises may involve performing multiple repetitions of an exercise with a greater ratio of activated slow twitch muscles to fast twitch muscles. In contrast, a power exercise involves performing one repetition of an exercise with a quick burst of energy and heavy use of fast twitch muscles.

In the example shown in FIG. 4, the amplitudes of the muscle activation level of the three controlled strength exercises have less variation than the muscle activation level of the power exercise. In particular, the muscle activation data for the power exercise has three amplitude peaks while the muscle activation data for each of the three controlled strength exercises have one amplitude peak. The muscle activation data for power exercises have more variability, for example, because the athlete performs power exercises over a shorter period of time, which may introduce transient peaks and/or more noise in the amplitude of the muscle activation data. A transient peak may be an outlier and not the true maximum muscle activation of the muscle. Thus, calibration engine 310 may generate more accurate calibration values based on the peak amplitudes from physiological data of controlled strength exercises. In some embodiments, the calibration engine 310 may exclude muscle activation data from power exercises (e.g., based on identifying the transient peaks) when generating calibration values. In another embodiment, the calibration engine 310 may generate more accurate calibration values by incorporating user information describing exercise context of the athlete, or information about the exercise corresponding to the physiological data (e.g., whether the exercise type is characteristic of strength controlled exercises or power exercises).

Figure 5:
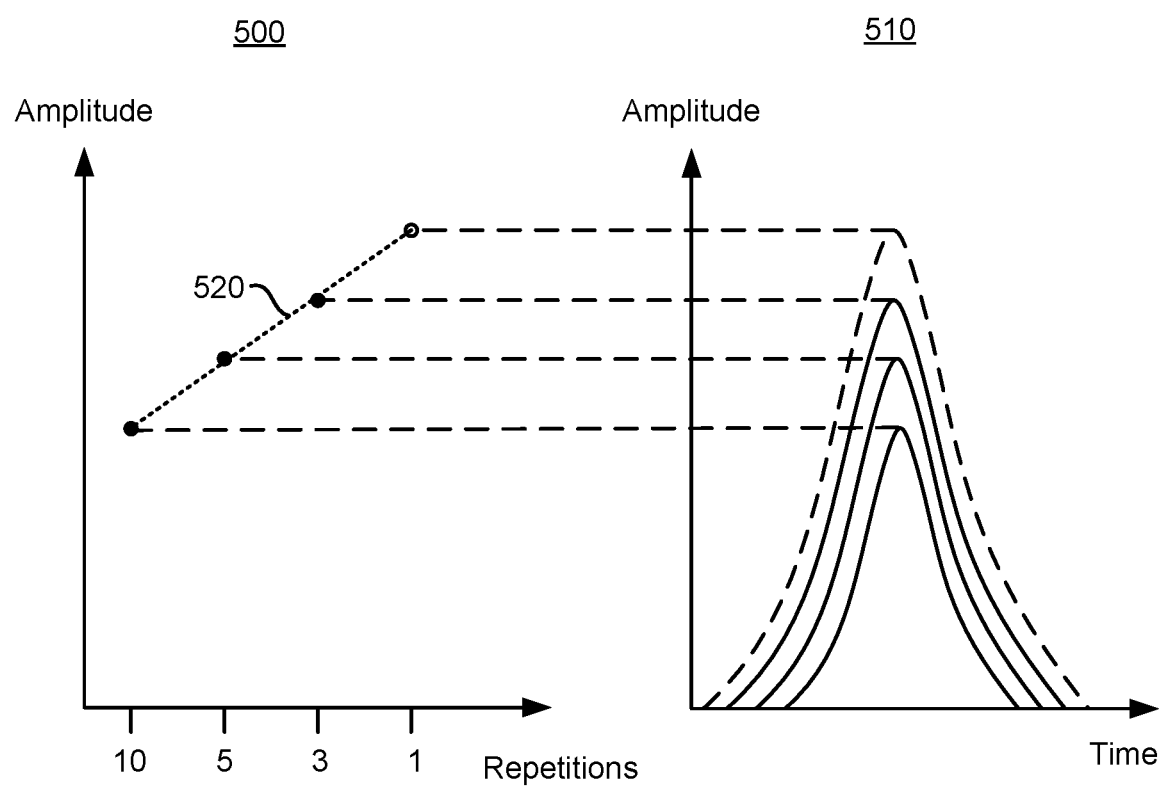
FIG. 5 shows graphs of physiological data based on a number of repetitions according to one embodiment.

FIG. 5 shows graphs of physiological data based on a number of repetitions according to one embodiment. In particular, the graph 500 includes data points indicating the repetition maximum amplitude of muscle activation levels associated with one, three, five, and ten repetitions (RM). The calibration engine 310 determines the repetition maximum amplitudes based on the muscle activation data shown in graph 510. In the example shown in FIG. 5, the repetition maximum amplitudes may be modeled as an approximately linear function dependent on the number of repetitions. Thus, the calibration engine 310 can use a linear regression model to predict repetition maximum amplitudes. For instance, the calibration engine 310 may not have physiological data associated with a one repetition maximum exercise, e.g., because it is unsafe for an athlete to perform only one repetition with a heavy weight before warming up for a workout. However, the calibration engine 310 can predict the one repetition maximum amplitude based on physiological data associated with three, five, and ten repetitions, as shown in the graphs 500 and 510. In other embodiments, the repetition maximum amplitude has a nonlinear relationship with the number of repetitions. The calibration engine 310 may also use a trained machine learning model to predict the one repetition maximum amplitude (e.g., in cases where a linear model is not suitable). The machine learning engine 320 trains the machine learning model using physiological data associated with other calibration exercises, e.g., with a variety of the number of repetitions for a set of a calibration exercise.

V. Example Confidence Level of Calibration

Figure 6A:
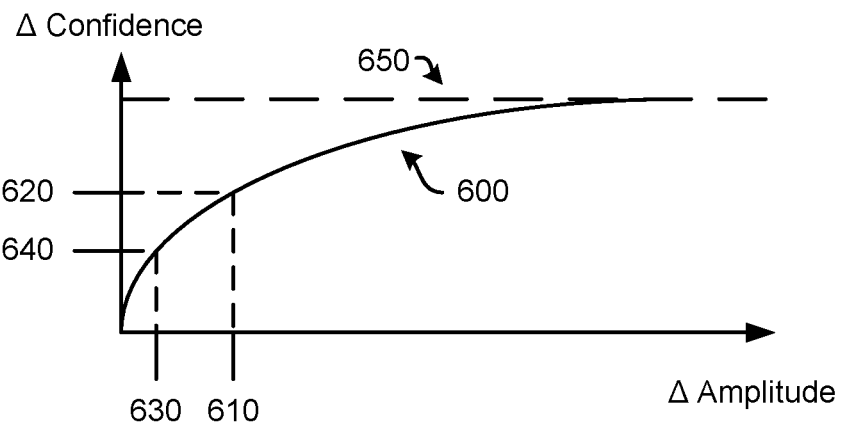
FIG. 6A shows a penalty function according to one embodiment.

FIG. 6A shows a penalty function 600 according to one embodiment. The penalty function 600 outputs a delta (e.g., difference or change) in confidence based on an input delta in amplitude. For example, the penalty function 600 outputs the deltas in confidence 620 and 640 based on input deltas in amplitude 610 and 630, respectively. Though the penalty function 600 shown in FIG. 6A is a logarithmic function that asymptotically approaches the confidence value 650, it should be noted that in other embodiments, the penalty function may be any other type of function, e.g., nonlinear, exponential, polynomial, arbitrary, periodic, etc. In some embodiments, the machine learning engine 320 trains a machine learning model that determines the penalty function 600. Alternatively, the calibration data store 340 may include a predetermined penalty function 600. In some embodiments, the exercise feedback system 100 uses a rule-based model or another type of model other than a machine learning model.

Figure 6B:
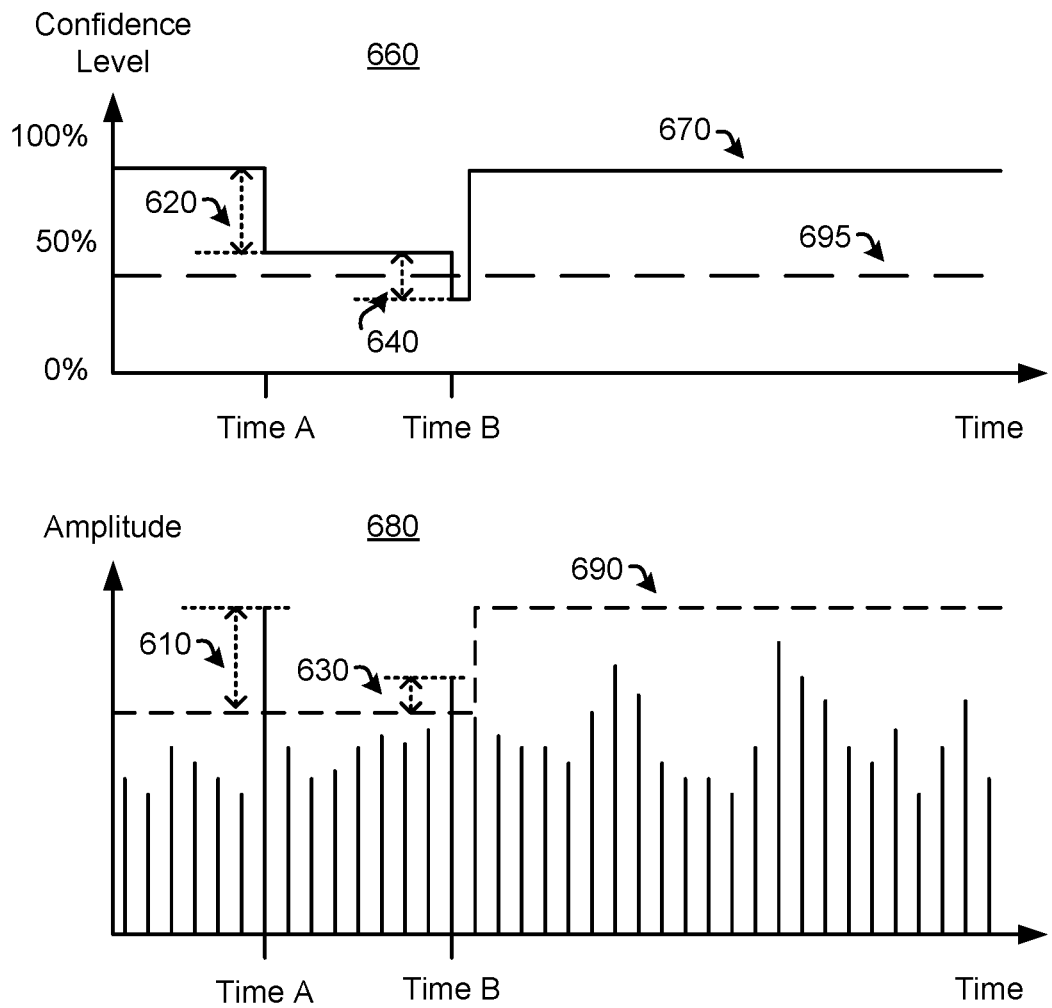
FIG. 6B shows a graph of a confidence level of physiological data generated by sensors over time according to one embodiment.

FIG. 6B shows a graph 660 of a confidence level 670 of physiological data generated by sensors over time according to one embodiment. In one embodiment, the machine learning engine 320 trains a machine learning model that determines and updates the confidence level 670 based on the physiological data and the penalty function 600 shown in FIG. 6A. The machine learning model determines an initial value for the calibration value 690 and for the corresponding confidence level 670 (e.g., 90%), which may be based on data from a calibration exercise or a reference calibration values. The calibration value 690 represents the predicted maximum muscle activation level of an athlete. As the athlete performs exercises, the exercise feedback system 100 receives physiological data, e.g., muscle activation data, generated by the sensors of the garment. The graph 680 illustrates the amplitude of the muscle activation data over time.

At time A, the muscle activation data has an amplitude greater than the calibration value 690 by a delta in amplitude 610. Using the penalty function 600, the machine learning model determines that the delta in amplitude 610 is mapped to the delta in confidence 620. Thus, the machine learning model decreases the confidence level 670 by the delta in confidence 620. Similarly, at time B, the muscle activation data has an amplitude greater than the calibration value 690 by a delta in amplitude 630. Using the penalty function 600, the machine learning model determines that the delta in amplitude 630 is mapped to the delta in confidence 640. Thus, the machine learning model decreases the confidence level 670 by the delta in confidence 640.

Over time, the machine learning model's confidence in the calibration value 690 can be eroded because amplitudes of data samples of the muscle activation data exceed the current calibration value 690. After time B, the machine learning model determines that the confidence level 670 is less than an adjustable threshold confidence level 695, e.g., 40%. In response to this determination, the machine learning model updates the calibration value 690, for example, by increasing the calibration value 690 to the maximum amplitude of muscle activation received for the athlete. Alternatively, the machine learning model may update the calibration value 690 by a percentage of the current calibration value 690 (e.g., increase by 10%), or by a predetermined constant value. In one embodiment, the machine learning model adjusts the threshold confidence level 695 to modify the frequency at which the calibration value 690 is updated. In particular, by increasing the threshold confidence level 695, the confidence level 670 is more likely to fall under the threshold confidence level 695, and thus the machine learning model will update the calibration value 690 more frequently. However, updating the calibration value 690 too frequently may confuse the athlete, so the machine learning model may determine an upper limit for the threshold confidence level 695, as well as a lower limit to avoid not updating the calibration value 690 frequently enough. In some embodiments, the machine learning model updates the calibration value 690 after the athlete has performed a certain number of exercises.

In some embodiments, the machine learning model learns to optimize how frequently the calibration value 690 is updated. For example, the machine learning model determines a number of repetitions or sets of exercises to include in a calibration routine having one or more calibration exercises. The machine learning model can also determine a number of sets or exercises that the athlete completes subsequent to completing the calibration routine before updating the calibration value for the first time. Similarly, the machine learning model can also determine a number of sets or exercises that the athlete completes subsequent to the previous calibration value update before the next update of the calibration value. For penalty functions that are exponential-type functions with a time constant, the machine learning model may optimize the time constant to avoid eroding confidence in the calibration value too conservatively or too aggressively, e.g., resulting in calibration value updates that are not frequent enough or too frequent.

The machine learning model learns to optimize how frequently the calibration value 690 is updated based on training sets derived using physiological data and user information from other athletes of the exercise feedback system 100. For example, the machine learning model has a target frequency of updating a calibration value no more than once a week. Further, the machine learning model determines an initial value for the calibration value for athletes who are 15-25 year old male basketball players. A training set indicates that for a population of 15-25 year old male basketball players, the calibration engine 310 updated the calibration value twice a week, which is twice as frequent as the target frequency of no more than once a week. For instance, the maximum amplitude of muscle activation levels for the population of athletes was frequently greater than the machine learning model originally predicted. Accordingly, the machine learning model trained using this training set learns that the initial value was likely too low because the calibration engine 310 kept increasing the calibration value. When determining a calibration value for a subsequent athlete who has similar (or the same) characteristics as the population of 15-25 year old male basketball players, the machine learning model determines a new calibration value that is greater than the initial value, e.g., to be more conservative in the prediction. On the other hand, if the training set indicates that the calibration value was updated less frequently than the target frequency, the machine learning model determines a new calibration value that is less than the initial value, e.g., to be more aggressive in the prediction.

Along with updating the calibration value 690 after time B, the machine learning model also updates the confidence level 670, e.g., increasing the confidence level 670 to 90%. The confidence level 670 increases when the calibration value 690 is updated because the machine learning model is more certain of the new prediction of the calibration value 690. In some embodiments, the machine learning model waits a predetermined period of time after time B to update the calibration value 690. For instance, the machine learning model waits until after the athlete has completed the current set of exercises (or waits until the next day) before updating the calibration value 690 so that the biofeedback provided to the user during the set appears more stable to the athlete.

In some embodiments, the machine learning model periodically updates calibration values over time. For example, the machine learning model increases the predicted maximum amplitude of an athlete's muscle activation levels once a month to account for the athlete's muscle growth. In other words, as the athlete performs strength training, the athlete should be progressing and able to lift heavier weights. As another example, during a given set of exercises, the machine learning model may decrease the predicted maximum amplitude of an athlete's muscle activation levels to account for fatigue or freshness (e.g., when the athlete is starting a workout after a period of rest). Due to fatigue, the athlete may not be able to lift as heavy weights on a repetition toward the end of a set in comparison to a repetition toward the start of the set.

After the machine learning model updates the calibration value 690, the biofeedback engine 330 generates biofeedback for the athlete based on the updated calibration value 690. Thus, the biofeedback is more likely to accurately represent the performance of the athlete because the biofeedback is based on a more accurate predicted maximum value. In some embodiments, the biofeedback engine 330 retroactively updates previously generated biofeedback. For example, a sample biofeedback indicates that the athlete exerted the athlete's quadriceps muscles at 110% muscle activation level. After the machine learning model updates the calibration value 690 to a greater value, the biofeedback engine 330 updates the sample biofeedback to now indicate that the athlete exerted the athlete's quadriceps muscles at 90% muscle activation level. The percentage of muscle activation level decreases because the calibration value 690 increases, e.g., representing a greater predicted maximum muscle activation level.

As another example, the calibration engine 310 generates a first set of calibration values for an athlete's glutes and biceps muscles based on physiological data from calibration exercises performed by the athlete during an onboarding process. Based on the first set of calibration values, the biofeedback engine 330 generates biofeedback comparing the performance of the athlete's glutes and biceps. The biofeedback engine 330 provides the comparative biofeedback during a period of time as the athlete performs additional workouts. At a future time, the calibration engine 310 generates a second set of calibration values for the athlete including an updated calibration value for the biceps muscles. The biofeedback engine 330 may reprocess the biofeedback based on the second set of calibration values to update the previously provided comparative biofeedback during the period of time. Thus, the updated comparative biofeedback may more accurately compare the performance of the athlete's glutes and biceps muscles, and may be more consistent with subsequent biofeedback generated based on the second set of calibration values.

VI. Example Process Flow

Figure 7:
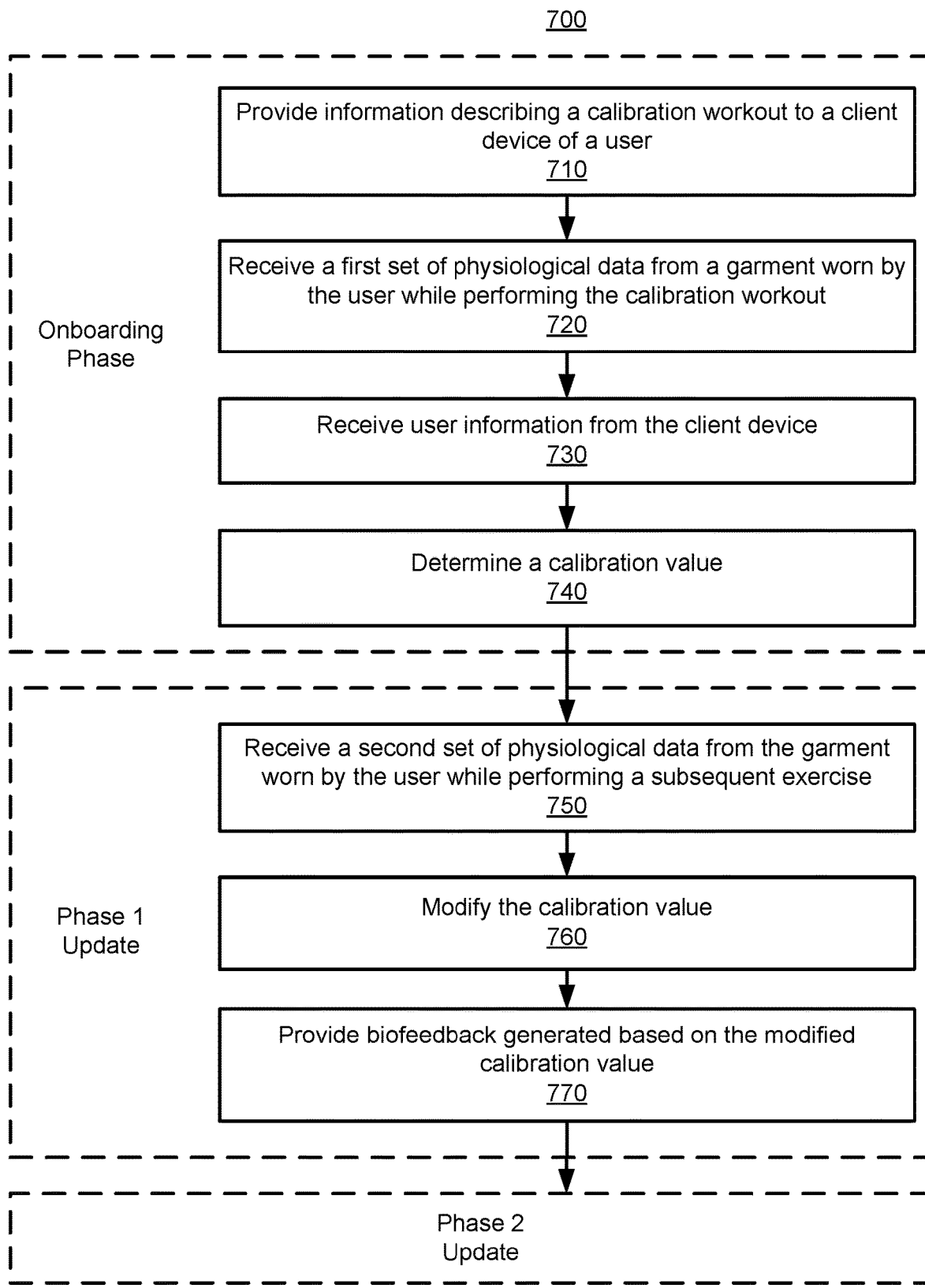
FIG. 7 is a flowchart of a process for calibrating the exercise feedback system according to one embodiment.

FIG. 7 is a flowchart of a process 700 for calibrating an exercise feedback system according to one embodiment. In some embodiments, the process 700 is performed by the exercise feedback system 100—e.g., modules of the exercise feedback system 100 described with reference to FIG. 3A—within the system environment in FIG. 1. The process 700 may include different or additional steps than those described in conjunction with FIG. 7 in some embodiments or perform steps in different orders than the order described in conjunction with FIG. 7.

In one embodiment, the calibration engine 310 provides 710 information describing a calibration workout to a client device 110 of a user (e.g., an athlete). The calibration workout may be part of an onboarding process completed by the athlete when the athlete begins using the exercise feedback system 100 with an athletic garment 130, e.g., for the first five workouts of the athlete. The calibration engine 310 may provide the athlete with multiple options of muscle groups to calibrate. Based on the athlete's selection, the calibration engine 310 may provide the athlete with multiple options of exercises suitable for calibrating the selected muscle group, e.g., a biceps curl exercise and a pull-up exercise are provided as options for calibrating the biceps muscle group. The calibration workout may include one or more sets of exercises, where each exercise may include any number of repetitions. In one embodiment, the calibration workout includes at least two sets of an exercise for a given muscle, and the repetition maximum is different for at least two sets.

The data processing engine 300 receives 720 a first set of physiological data from a garment 130 worn by the user while performing the calibration workout. The physiological data is generated by sensors of the garment 130 and describes muscle activation of one or more muscles of the user. The calibration engine 310 receives 730 user information from the client device 110. The user information may include, for example, demographic data, performance metrics, a user perceived effort corresponding to the calibration workout, etc. In one embodiment, the user perceived effort indicates a first effort level of a first set of an exercise of the calibration workout, and indicates a second effort level of a second set of the exercise (e.g., the first effort level is 50% and the second effort level is 75%), where the two sets may have a different number of repetitions.

The calibration engine 310 determines 740 a calibration value based at least in part on the first set of physiological data and the user information. In some embodiments, the calibration engine 310 determines the calibration value based on the first set of physiological data without requiring user information. Thus, in such embodiments, the calibration engine 310 does not necessarily receive the user information during the onboarding process. In other embodiments, the calibration engine 310 determines the calibration value based on the user information without requiring the first set of physiological data. Thus, in such embodiments, the calibration engine 310 does not necessarily receive the first set of physiological data during the onboarding process. In some embodiments, the data processing engine 300 determines a level of data quality of the physiological data based on bioimpedance data received from the sensors; the calibration engine 310 may determine calibration values further based on the level of data quality.

The data processing engine 300 receives 750 a second set of physiological data (e.g., also describing muscle activation of the user's muscles) from the garment 130 worn by the user while performing a subsequent workout. The calibration engine 310 modifies 760 the calibration value based on the second set of physiological data. The calibration engine 310 may modify the calibration value in response to determining that an amplitude of a data subset of the second set of physiological data is greater than the calibration value (e.g., the calibration value is an underestimate). In other embodiments, the calibration engine 310 may modify the calibration value in response to determining that an amplitude of a data subset of the second set of physiological data is less than the calibration value by a threshold value (e.g., the calibration value is an overestimate). For instance, if the calibration value is an underestimate, the calibration engine 310 increases the calibration value. On the other hand, if the calibration value is an overestimate, the calibration engine 310 decreases the calibration value. In some embodiments, the calibration engine 310 uses a penalty function and/or a trained machine learning model to modify the calibration value. In some embodiments, the calibration value is further determined or modified based on user information received from the client device 110. The user information may describe, e.g., the workouts, exercises, weight, reps, or other performance metrics of the athlete corresponding to the second set of physiological data.

The biofeedback engine 330 provides 770 biofeedback to the client device 110 for communication to the user, where the biofeedback is generated based on the modified calibration value. The biofeedback may indicate, e.g., a metric of athletic performance of the user, a level of balance of the user (e.g., comparing the effort level of the left and right biceps muscles), a level of workload of the user's muscles, or the contribution of a given muscle compared to an aggregate group of muscles. Since the exercise feedback system 100 can receive physiological data from any number of subsequent exercises, the calibration engine 310 can perform ongoing calibration (e.g., after the onboarding process in completed) when updated physiological data of the athlete is available.

Further, the biofeedback may be a representation of the calibration value and modifications to the calibration value over time, in some embodiments. In an example use case, the biofeedback may indicate strength progression or regression based on changes to the calibration value over a period of time. For example, an athlete's increase in strength may correspond to an increase in muscle fiber size, which results in an increase in the maximum signal response measured from a given muscle. The calibration engine 310 may modify the calibration value over time to represent an updated maximum signal response. In another example, the biofeedback includes a representation of a user profile and provides information indicating the relative strength of different muscle groups by comparing calibration values of different muscle groups. In another example, the exercise feedback system 100 provides biofeedback indicating balance information based on comparing calibration values corresponding to the right and left muscles of a symmetric muscle type. Biofeedback may also include a comparison of calibration values between different athletes.

In the embodiment shown in FIG. 7, steps 710-740 are part of the onboarding phase when the athlete performs calibration exercises. During the onboarding process, the calibration engine 310 determines an initial reference for calibration values, e.g., a "starting point." The calibration engine 310 can perform ongoing calibration in two or more phases. In particular, steps 750-770 are part of a phase 1 update, which is performed by the exercise feedback system 100 within a duration of time after the onboarding phase (e.g., five weeks or a month). The exercise feedback system 100 may repeat steps 750-770 as part of a subsequent phase 2 update performed after the phase 1 update. As the athlete continues to complete additional workouts, the exercise feedback system 100 may continue to refine the calibration by performing any number of additional phase 2 updates based on additional physiological data from the workouts.

In some embodiments, the exercise feedback system 100 optimizes parameters of the phase 1 process to account for a greater expected degree of error between the starting point calibration value after onboarding and the actual target calibration level for the user. For instance, during the phase 1 update process, the exercise feedback system 100 adjusts the calibration levels to accurately reflect the user, and thus the calibration value may be modified more frequently. Parameters of the phase 2 update process may be optimized to adjust to physiological changes of the user. Thus, the exercise feedback system 100 may be optimized to modify the calibration value less frequently during the phase 2 update process.

In some embodiments, the exercise feedback system 100 can perform a process including the ongoing calibration phase without necessarily including an onboarding calibration phase. For example, the exercise feedback system 100 retrieves default (or reference) calibration values or previously calibration values that are stored in the calibration data store 340. The exercise feedback system 100 may modify the retrieved calibration values based on updated physiological data from the athlete during the ongoing calibration phase.

Figure 8:
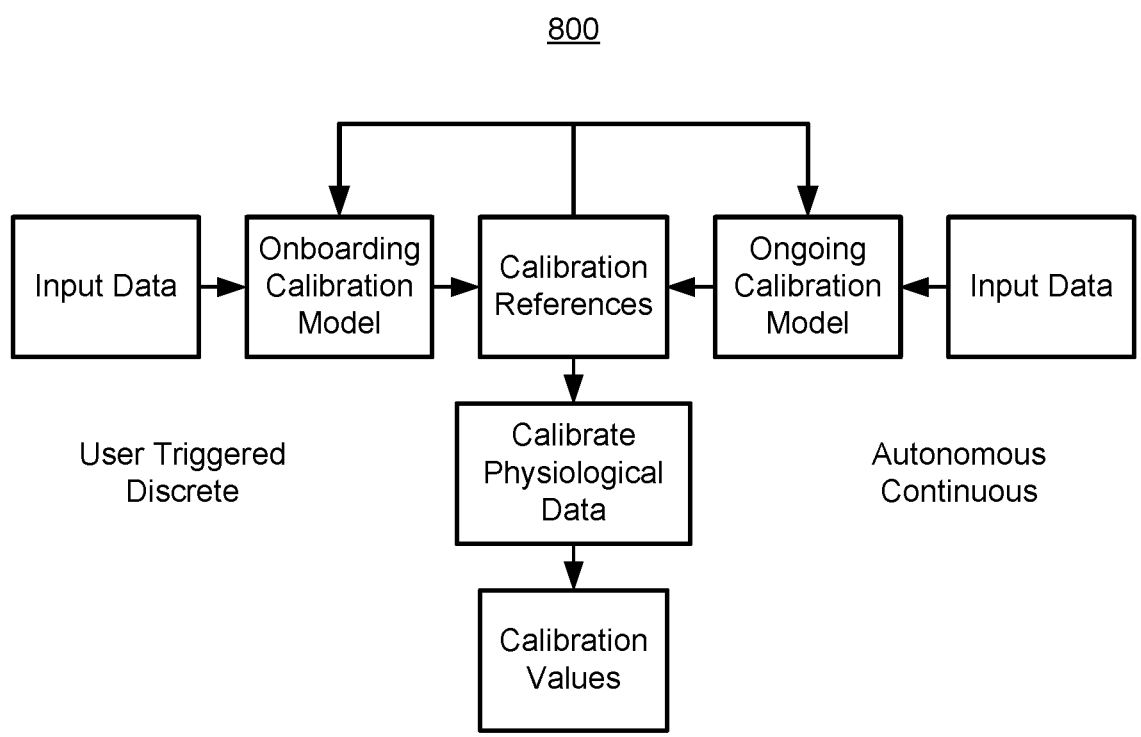
FIG. 8 is a diagram illustrating onboarding and ongoing calibration phases of the exercise feedback system according to one embodiment.

FIG. 8 is a diagram 800 illustrating onboarding and ongoing calibration phases of the exercise feedback system 100 according to one embodiment. As previously described, the exercise feedback system 100 can perform calibration during an onboarding phase and an ongoing phase. The machine learning engine 320 may train different models for each phase, e.g., an onboarding calibration model and an ongoing calibration model. Alternatively, the machine learning engine 320 may train one model for multiple phases. The models may be trained via machine learning techniques using feature sets, e.g., derived based on information from a population of athletes of the exercise feedback system 100. The feature sets may also include information such as physiological data of athletes associated with different associated repetition maxima, different target calibration values, different perceived effort levels, user information pertaining to demographics of the user, performance metrics of the user, or information about exercises completed by the user (e.g., type of exercise, reps, or weight).

In some embodiments, the models determine calibration references (e.g., initial calibration values) based on input data. Input data may include information input by the user such as demographic data (e.g., age, gender, height, weight), geographical location data, a perceived effort level for an exercise or workout, a performance metric (e.g., a personal record of the athlete), or other types of exercise content (e.g., number of repetitions, type of exercise, weight for the exercise, duration of the exercise, time of day, etc.). The input data may also be received by the exercise feedback system 100 without requiring manual input from the user. For instance, the exercise feedback system 100 uses an application programming interface (API) to receive input data from a third party system such as a social networking system. Differences in the input data, e.g., across different athletes, may manifest as variations in physiological data from the athletes.

Based on the calibration references, the calibration engine 310 calibrates physiological data and determines calibration values. The exercise feedback system 100 may perform a discrete onboarding calibration if triggered by the user, e.g., when the user begins using the exercise feedback system 100 for workouts or when the user provides updated input data. On the other hand, the exercise feedback system 100 may perform continuous ongoing calibration over time without manual input, that is, autonomously.

VII. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
receiving information from a client device of a user;
receiving a first set of physiological data from a garment worn by the user, the first set of physiological data describing muscle activation of a plurality of muscles of the user while performing a workout, the garment including a plurality of sensors configured to generate physiological data;
receiving a second set of physiological data from the garment worn by the user, the second set of physiological data describing muscle activation of the plurality of muscles of the user while performing a subsequent workout;
automatically refining a calibration value determined from the first set of physiological data, upon processing a second set of physiological data associated with the subsequent workout, wherein automatically refining the calibration value comprises:
for each of a set of time points spanning the subsequent workout:
comparing a confidence level in the calibration value to a threshold confidence level; and
upon determination that the confidence level in the calibration value fails to satisfy the threshold confidence level, automatically modifying the calibration value based on the second set of physiological data; and
providing biofeedback to the client device for communication to the user, the biofeedback generated based on the modified calibration value.

2. The method of claim 1, wherein the calibration value is further determined based on a perceived user effort corresponding to the workout.

3. The method of claim 1, wherein the workout comprises a calibration workout provided through the client device of the user, and wherein the first set of physiological data describes muscle activation of the user while performing the calibration workout.

4. The method of claim 3, wherein the calibration workout includes at least two sets of an exercise associated with at least one muscle of the plurality of muscles, the perceived user effort indicating a first effort level for a first set of the at least two sets, and a second effort level for a second set of the at least two sets, and wherein the calibration value is determined based on a calibration value model configured to generate the calibration value based on the first set of physiological data and the perceived user effort.

5. The method of claim 4, wherein the calibration value model is trained using data collected from a population of athletes including physiological data associated with different perceived effort levels and target calibration values.

6. The method of claim 3, wherein the calibration workout includes at least two sets of an exercise associated with at least one muscle of the plurality of muscles, the at least two sets including a first set of a first number of repetitions and a second set of a second number of repetitions, each of the first number of repetitions and the second number of repetitions associated with repetition maximums, and wherein the calibration value is determined based on a calibration value model configured to generate the calibration value based on the first set of physiological data.

7. The method of claim 6, where the calibration value model is trained using data collected from a population of athletes including physiological data associated with different associated repetition maxima and target calibration values.

8. The method of claim 6, wherein:
the exercise comprises one of: a kickback, a leg curl, a squat, a chest fly, a bent over row, an arm curl, an arm extension, and an arm raise; and
the at least one muscle of the plurality of muscles comprising at least one of: a gluteus maximus muscle, a hamstring muscle, a quadriceps muscle, a pectoral muscle, a biceps muscle, a triceps muscle, and a deltoids muscle.

9. The method of claim 1, wherein:
the calibration value is derived from a set of maximum amplitudes in muscle activation, across a set of repetitions of an exercise of at least one of the workout and the subsequent workout, for at least one of the plurality of muscles.

10. The method of claim 9, further comprising predicting a single-repetition maximum amplitude in muscle activation from the set of repetition maximum amplitudes.

11. The method of claim 1, further comprising:
receiving bioimpedance data from the plurality of sensors of the garment, wherein the calibration value is further determined based on the bioimpedance data.

12. The method of claim 11, further comprising:
determining a level of data quality for each of the first set of physiological data and the second set of physiological data based on the bioimpedance data, wherein the calibration value is further determined based on the levels of data quality.

13. The method of claim 1, further comprising:
receiving heart rate information of the user generated by at least one sensor of the plurality of sensors, wherein the calibration value is further determined based on the heart rate information.

14. The method of claim 1, further comprising:
determining a difference between an amplitude of a data subset of the second set of physiological data and the calibration value; and
modifying the confidence level based on the difference of the amplitude of the data subset and the calibration value.

15. The method of claim 14, wherein:
the confidence level is modified based on a non-linear function that generates a confidence level value based on the difference of the amplitude of the data subset and the calibration value; and
modifying the confidence level includes reducing the confidence level by the confidence level value.

16. The method of claim 14, wherein:
the confidence level is modified based on a machine learning model that generates a confidence level value based on the difference of the amplitude of the data subset and the calibration value, the machine learning model trained using feature vectors based on physiological data associated with a population of users that perform exercises; and modifying the confidence level includes reducing the confidence level by the confidence level value.

17. The method of claim 1, wherein the biofeedback indicates at least one of: (i) a level of exertion of at least one muscle of the plurality of muscles of the user while performing the subsequent workout, (ii) a level of balance of the user while performing the subsequent workout, (iii) a level of workload of the plurality of muscles while performing the subsequent workout, (iv) a first contribution of a given muscle of the plurality of muscles compared to a second contribution of the plurality of muscles while performing the subsequent workout, and (v) a strength progression or regression based on changes to the calibration value over time.

18. The method of claim 1, further comprising modifying additional biofeedback information based on the modified calibration value, the additional biofeedback information based on the calibration value before it was modified.

19. The method of claim 1, wherein the user information describes at least one of: a performance metric of the user, exercises corresponding to the first or second set of physiological data, and another set of physiological data corresponding to a group of other users.

20. The method of claim 1, wherein the user information is received from a third party application associated with the client device of the user.

21. A computer program product comprising a non-transitory computer readable storage medium having instructions encoded thereon that, when executed by a processor, cause the processor to:

provide information describing a calibration workout to a client device of a user;

receive a first set of physiological data from a garment worn by the user, the first set of physiological data describing muscle activation of a plurality of muscles of the user while performing the calibration workout, the garment including a plurality of sensors configured to generate physiological data;

receive user information from the client device;

receive a second set of physiological data from the garment worn by the user, the second set of physiological data describing muscle activation of the plurality of muscles of the user while performing a subsequent workout;

automatically refine a calibration value determined from the first set of physiological data, upon processing a second set of physiological data associated with the subsequent workout, wherein automatically refining the calibration value comprises:

for each of a set of time points spanning the subsequent workout:

compare a confidence level in the calibration value to a threshold confidence level; and upon determination that the confidence level in the calibration value fails to satisfy the threshold confidence level, automatically modify the calibration value based on the second set of physiological data; and provide biofeedback to the client device for communication to the user, the biofeedback generated based on the modified calibration value.

* * * * *